United States Patent [19]

Hesse

[11] Patent Number: Plant 6,935

[45] Date of Patent: Jul. 18, 1989

[54] CHRYSANTHEMUM PLANT NAMED BLUES

[75] Inventor: Peter S. Hesse, Bradenton, Fla.

[73] Assignee: Ball Seed Company, West Chicago, Ill.

[21] Appl. No.: 139,764

[22] Filed: Dec. 30, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Blues having pink ray florets, immature disc florets comprising a generally greyed orange outer ring and a dark purple eye in the center, with the eye fading during maturity to a light pink; 7 week flower response, anemone flower type, compact semi-upright growth habit, and its free branching and profuse flowering.

1 Drawing Sheet

The present invention comprises a new and distinct cultivar of *Chrysanthemum morifolium,* hereinafter referred to by the cultivar name Blues.

Blues is a product of a planned breeding program which has the objective of creating new Chrysanthemum cultivars having compact growth habit, early flowering response, anemone flower form, and suitability for use as a garden mum. Such traits in combination were not present or needed improvement in previously available commercial cultivars.

Blues was originated from a hybridization made by applicant in a controlled breeding program in Parrish, Fla., in 1984. The female parent was Viva. The male parent of Blues was Volunteer. Blues was discovered and selected as one flowering plant within the progeny of the stated parentage by applicant in November 1984 in a controlled environment in Parrish, Fla.

The first act of asexual reproduction of Blues was accomplished when vegetative cuttings were taken from the initial selection in March 1985 in a controlled environment in Parrish, Fla. by a technician working under formulations established and supervised by applicant. Horticultural examination of selected units initiated in September 1985 has demonstrated that the combination of characteristics as herein disclosed for Blues are firmly fixed and are retained through successive generations of asexual reproduction.

The following traits have been repeatedly observed and are determined to be basic characteristics of Blues, which in combination distinguish this Chrysanthemum as a new and distinct cultivar:

1. Seven week flower response.
2. Pink ray florets.
3. Immature disc florets display a round deep purple "dark eye" in center, which fades to light pink as disc florets mature. Disc florets surrounding the eye are greyed orange in color, thereby providing a unique contrast at the center of the flower. These disc florets also fade as flower matures. When grown under very high temperatures, the eye may be absent altogether.
4. Anemone flower type.
5. Ray florets are flat and up to 2.5 cm long and 7 mm wide.
6. Disc florets are funnelform and up to 12 mm long.
7. Total flower diameter reaches 5.5 cm.
8. Compact semi-upright growth habit.
9. Freely branching and profuse flowering.

10. Suitable for use as a garden mum for production in 4½" to 1 gallon containers.

Blues has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Blues is Carmella. In comparison to Carmella, Blues has pink ray floret color and a dark, deep purple eye in the center of the immature disc; one week earlier flower response, and a more compact growth habit. The flower size and form of Blues are similar to those same characteristics of Carmella.

The accompanying photographic drawing shows typical inflorescence and foliage characteristics of Blues, with colors being as nearly true as possible with illustrations of this type. The photographic drawing comprises a black and white photograph, with two flowers being colored to accurately depict the true color of the ray and disc florets of Blues prior to flower maturation.

In the following description, color references are made to The Royal Horticultural Society Colour Chart. The color values were determined between 2:00 and 2:30 p.m. on Oct. 21, 1987 under fluorescent light at Parrish, Fla.

Classification:

*Botanical.*—*Chyrsanthemum morifolium,* cv. Blues.
*Commercial.*—Anemone garden mum.

INFLORESCENCE

A. Capitulum:
*Form.*—Flat.
*Type.*—Anemone.
*Diameter across face.*—Up to 5.5 cm.

B. Corolla of ray florets:
*Color (general tonality from a distance of three meters).*—Pink.
*Color (upper surface).*—73A.
*Color (under surface).*—73D.

C. Corolla of disc florets:

*Color* (*immature*).—163B around edge of disc, 187A in center.

*Color* (*mature*).—The eye in center and the surrounding ring fade to a light pink, approximately 73D.

D. Reproductive organs:

*Androecium.*—Present in disc florets only.

*Gynoecium.*—Present in both disc and ray florets.

PLANT

A. General appearance:

*Height.*—21 cm when grown in the ground, given no long days and one pinch. Height will vary depending upon growing conditions.

B. Foliage:

*Color* (*upper surface*).—147A.

*Color* (*under surface*).—147B.

*Shape.*—Ovate, deeply lobed and serrate.

I claim:

1. A new and distinct cultivar of Chrysanthemum plant named Blues, as illustrated and described.

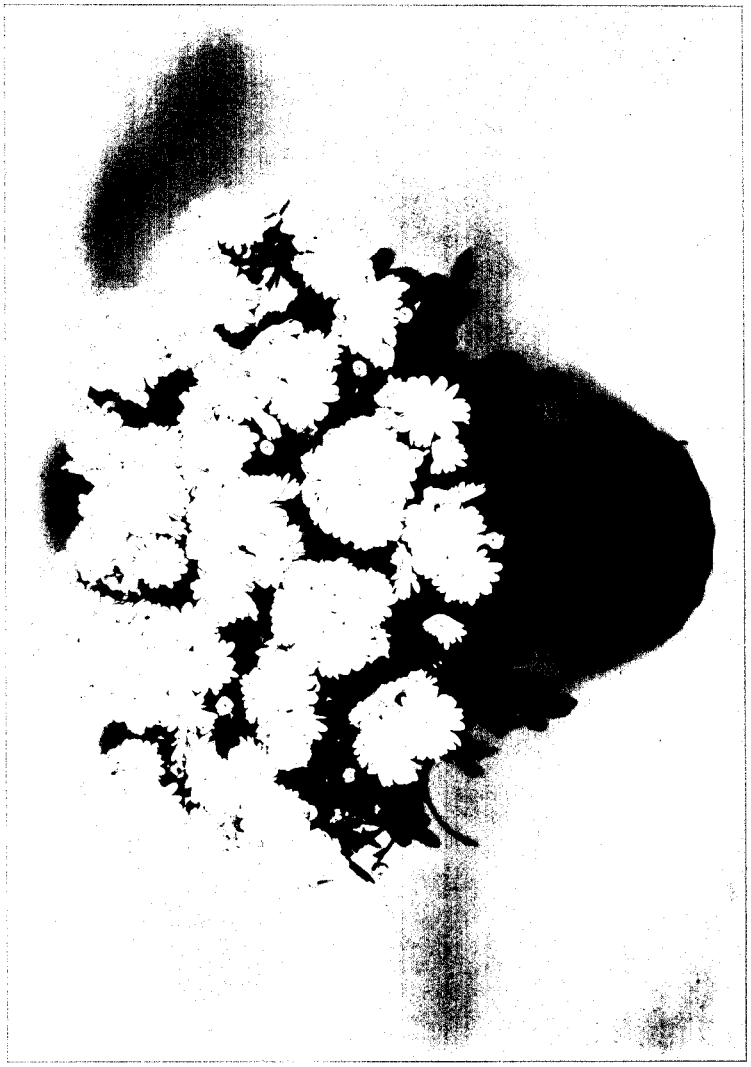

* * * * *